(12) United States Patent
Kinnunen et al.

(10) Patent No.: US 6,537,227 B2
(45) Date of Patent: Mar. 25, 2003

(54) METHOD AND EQUIPMENT FOR HUMAN-RELATED MEASURING

(75) Inventors: Hannu Kinnunen, Oulu (FI); Seppo Nissilä, Oulu (FI)

(73) Assignee: Polar Electro Oy, Kempele (FI)

( * ) Notice: Subject to any disclaimer, the term of this patent is extended or adjusted under 35 U.S.C. 154(b) by 48 days.

(21) Appl. No.: 09/798,577

(22) Filed: Mar. 2, 2001

(65) Prior Publication Data

US 2001/0023320 A1 Sep. 20, 2001

(30) Foreign Application Priority Data

Mar. 7, 2000 (FI) .................................................. 000522

(51) Int. Cl.[7] .................................................. A61B 5/02
(52) U.S. Cl. .................... 600/500; 600/483; 600/508
(58) Field of Search ............................... 600/500, 481, 600/483, 485, 501, 502, 503, 508, 509

(56) References Cited

U.S. PATENT DOCUMENTS

| | | | |
|---|---|---|---|
| 4,566,461 A | * | 1/1986 | Lubell et al. ............... 377/24.2 |
| 5,297,558 A | | 3/1994 | Acorn et al. |
| 5,640,956 A | * | 6/1997 | Maeyama .................. 600/502 |
| 5,853,351 A | | 12/1998 | Maruo et al. |
| 5,976,083 A | * | 11/1999 | Richardson et al. ........... 482/8 |
| 6,287,262 B1 | * | 9/2001 | Amano et al. ............... 600/300 |
| 6,361,502 B1 | * | 3/2002 | Puolakanaho et al. ...... 600/502 |

FOREIGN PATENT DOCUMENTS

| | | |
|---|---|---|
| EP | 0 845 241 A1 | 6/1998 |
| JP | 8052119 | 2/1996 |

* cited by examiner

*Primary Examiner*—Max F. Hindenburg
*Assistant Examiner*—Navin Natnithithadha
(74) *Attorney, Agent, or Firm*—Hoffmann & Baron, LLP

(57) ABSTRACT

A heart rate measuring arrangement comprising measuring means (500A to 500B) for measuring a person's heart rate during exercise and a calculating unit (532) for calculating an assessment of the person's energy consumption during exercise using at least two calculating parameters, one of which is a heart rate parameter included in the person's measured heart rate information, the heart rate measuring arrangement further comprising presenting means (530) for presenting the formed assessment of the person's energy consumption. The calculating unit is arranged to use an energy consumption reference value as a calculating parameter, which reference value is obtained by using one or more performance parameters representing the person's physical performance.

31 Claims, 5 Drawing Sheets

METHOD AND EQUIPMENT FOR HUMAN-RELATED MEASURING

FIELD OF THE INVENTION

The invention relates to exercise and sports, in particular to applications in which human energy consumption is measured in connection with exercise.

BACKGROUND OF THE INVENTION

To determine energy consumption in connection with exercise is important when planning a correct relation between an athlete's nutrition and intensity of exercise. An exercise of excessive duration, for instance, may deplete the person's energy reserves to a disadvantageous level. Further, if the objective is to lose weight, it is important to obtain information on the amount of energy consumed during exercise.

Intensity of a workout or exercise can be described by means of the person's heart rate. The heart rate represents the heart beat frequency in a time unit, the unit being e.g. beats per minute. Sports and exercise increase the heart muscle mass and the capability of the system to supply oxygen to the body. The heart's capability to pump oxygenated blood into the body improves, and consequently by one contraction, i.e. beat, the heart is able to pump a larger amount of blood in the body, whereby the beat rate can be lower than that of an unfit person. The person's heart rate during exercise is measured with a heart rate monitor, for instance. The heart rate monitor is a device that measures heart rate, for instance, on the chest from an electric signal transmitted by the heart and displays the measured heart rate on its display. The heart rate monitors often comprise a plurality of other facilities apart from the heart rate measurement, such as assessment of energy consumption during exercise. In prior art heart rate monitors energy consumption has been assessed on the basis of the heart rate and the person's weight, gender and age, for instance.

Hence, it is clear that the prior art heart rate monitors assessing energy consumption have a significant disadvantage. The method does not take into account that a fit person performs a larger amount of work at a given heart rate level than an unfit person, whereby the amount of energy consumed by the fit person is larger than that of the unfit person.

BRIEF DESCRIPTION OF THE INVENTION

The object of the invention is to provide an improved method and equipment implementing the method for assessing energy consumption during exercise. This is achieved by the method described below. This is a method for assessing a person's energy consumption during exercise. The method provides an assessment of the person's energy consumption by means of at least two calculating parameters, one of which is a heart rate parameter during exercise measured from the person's heart rate information. As one calculating parameter the method employs an energy consumption reference value which is obtained by using one or more performance parameters representing the person's physical performance.

The invention also relates to a heart rate measuring arrangement comprising measuring means for measuring a person's heart rate during exercise and a calculating unit for calculating an assessment of the person's energy consumption during exercise using at least two calculating parameters, one of which is a heart rate parameter included in the person's measured heart rate information, the heart rate measuring arrangement further comprising presenting means for presenting the formed assessment of the person's energy consumption. The calculating unit is arranged to use an energy consumption reference value as a calculating parameter, which reference value is obtained by using one or more performance parameters representing the person's physical performance.

The preferred embodiments of the invention are disclosed in the dependent claims.

The invention thus relates to a method and equipment for assessing a person's energy consumption during exercise. In the description of the invention, the exercise refers to a physical exercise that is performed at a higher heart rate level than the resting heart rate. Broadly speaking, the invention relates to assessing human energy consumption as the heart rate level exceeds 80 beats per minute.

According to the method of one preferred embodiment of the invention, equipment implementing the method, such as a heart rate monitor, is personally set for each performer of exercise in a personalizing phase of the method. The personalizing phase is preferably performed prior to the exercise and in that step an assessment is made of the person's physical condition, which assessment is utilized in assessing the energy consumption on the basis of the heart rate information during the exercise. An advantage with this is that it takes into account the fact that at a given heart rate level a fit person consumes more energy than an unfit person. The physical condition is described by the maximum performance parameter value, such as the maximal oxygen uptake value, maximum value of running or swimming speed, maximum performance when pedalling an exercise bike or the like.

In one preferred embodiment of the invention, interdependence between the person's heart rate and energy consumption is determined in a personalizing phase by means of a performance parameter, such as oxygen uptake. First, a maximum value of oxygen uptake is formed at an upper heart rate level, which preferably is the maximum heart rate level corresponding to the person's maximum performance. On the basis of the formed maximum value of oxygen uptake it is possible to form a maximum value of energy consumption representing the person's maximal energy consumption in accordance with the known principles of human physiology. The upper heart rate level allows to form a lower heart rate level, whose lower energy consumption is correspondingly formed by means of the maximum energy consumption. Between the formed upper heart rate level and the lower heart rate level, there is substantially linear dependence between the heart rate and the energy consumption.

According to another preferred embodiment, an intermediate heart rate level is designated between the lower heart rate level and the upper heart rate level, whereby the interdependence of the heart rate and the energy consumption is piecewise linear comprising linear interdependences between the lower and intermediate heart rate levels and the intermediate and upper heart rate levels respectively. The use of intermediate heart rate level allows to precise the actual energy consumption values. It is clear that the method of the invention may comprise a plurality of intermediate heart rate levels. It is clear that the physiological dependence between the heart rate and the energy consumption is not an exact linear dependence. In the above-described embodiments the expression substantially linear refers to dependences that are within a 10% range of variation in either direction with respect to the linear dependence, being e.g. piecewise linear or curve forms of higher degree.

The upper heart rate level to be used in forming the maximum value of the performance parameter is preferably the maximum heart rate level that can be generated, for instance, by assessing, calculating by a formula (220–age), measuring the heart rate corresponding to the maximum workload, or by forming an assessment of the maximum heart rate level by means of a neural network model, into which at least one physiological parameter of the person, such as age, weight, height, gender or the like, is entered as an input parameter.

The maximum value of the performance parameter corresponding to the upper heart rate level is formed, for instance, by measuring during exercise stress or by means of a neural network model. In one preferred embodiment of the invention, the neural network model is such that one or more heart rate parameters obtained from heart rate information, one or more physiological parameters and one or more exercise stress parameters are entered therein as input parameters. In one embodiment of the invention, a reference exercise is performed in the personalizing phase, the above exercise stress parameters then referring to parameters representing the workload of the reference exercise, such as resistance of an exercise bike, swimming speed, running speed or the like. On the basis of the known physiological formulae determining the interdependence of breathing gases and energy consumption it is possible to calculate the energy consumption value corresponding to the maximum value of the performance parameter, whereby the dependence between the heart rate and the energy consumption at the upper heart rate level is obtained. If a variable representing performance or speed is used as the performance parameter, the energy consumption is given by a formula having the structure: performance/speed * weight * constant, the constant determining the person's efficiency in exercise, for instance.

The lower heart rate level is formed from the upper heart rate level, for instance, by calculating about 50 to 60% of the maximum heart rate level. The lower heart rate level is selected such that the dependence between the heart rate and the energy consumption is known at heart rate levels exceeding the lower level, i.e. the dependence is linear or at least piecewise linear. The energy consumption corresponding to the lower heart rate level is obtained from the maximum energy consumption corresponding to the maximum heart rate, for instance, by calculating about 40% of the maximum energy consumption. If one intermediate heart rate level is used, the intermediate heart rate level is about 80% of the maximum heart rate and the energy consumption is about 75% of the maximum energy consumption.

In the use phase of the method, i.e. during an exercise, an assessment of energy consumption is formed by means of at least two calculating parameters. One of the calculating parameters is the person's heart rate during exercise. Instead of or in addition to the heart rate, it is also possible to use any other heart rate variable describing the workload of the performance, such as the standard deviation of the heart rate. In assessing energy consumption, one calculating parameter is one or more energy consumption reference values, such as maximum energy consumption, lower energy consumption, intermediate energy consumption, generated in the personalizing phase. Further, one embodiment employs one or more of the following variables as a calculating parameter: upper heart rate level, lower heart rate level, intermediate level.

In one embodiment of the invention equipment implementing the method of the invention is a heart rate monitor. The heart rate monitor is a device employed in sports, which measures human heart rate information either from an electrical impulse transmitted by the heart or from the pressure produced by the heart beat on an artery, or optically from blood flow in a blood vessel. Heart rate monitors have a variety of different structures, but the invention is not restricted to any particular heart rate monitor type. For instance, the heart rate monitor can be such that it comprises an electrode belt to be fitted around the user's chest measuring the heart rate by means of two or more electrodes. The electrode belt transmits the measured heart rate information inductively to a wrist-worn receiver unit. On the basis of the received magnetic pulses, the receiver unit calculates the heart rate and, when needed, other heart rate variables, such as moving standard deviation of the heart rate. The receiver unit, i.e. the wrist monitor, often includes a display for displaying the heart rate information or other parameters generated in the heart rate monitor. In connection with the present invention, variables, such as cumulative consumed energy or consumed energy per time unit, representing energy consumption during exercise are preferably presented on the display. Advantageously, the heart rate monitor also comprises means for entering user-specific physiological information as well as workload and exercise information. The entering means can be, for instance, a keypad of the heart rate monitor, display equipment that supports control, speech control, a telecommunication port for external control, or the like. In the above-described situation, the heart rate monitor refers to a whole formed by the electrode belt and the receiver unit.

The heart rate monitor can also be a one-piece device, i.e. such that also the presenting means are located on the chest, whereby there is no need to transmit the information to a separate receiver unit. Further, the structure of the heart rate monitor can be such that it comprises only a wrist-worn monitor which operates without the electrode belt to be fitted around the chest measuring the heart rate information from the vessel pressure or optically. In the description of the invention, the heart rate measuring arrangement refers to the above-described heart rate monitor solutions. The heart rate measuring arrangement also comprises the solutions, in which heart rate information is transmitted to an external computer or to a data network, which has presenting means, such as a computer screen, for presenting the information measured or generated by the heart rate monitor. In one embodiment the heart rate and energy consumption information during exercise is stored in a memory of the heart rate monitor and downloaded later on by an external computer.

In the case of a two-piece heart rate monitor the functions required by the method of the invention are preferably performed in the receiver unit. One or more mathematical models, such as a neural network, according to the invention and other functions required by the models are preferably implemented by means of software for a general-purpose processor of the receiver unit. The models and the functions can also be implemented as ASIC, by separate logic components or in any other corresponding manner.

An improved method for assessing energy consumption during exercise is achieved as an advantage of the invention. The method has an advantage that in the assessment of energy consumption the person's physical condition is taken into account. A further advantage is that the person's maximum heart rate and the corresponding energy consumption value are taken into account.

BRIEF DESCRIPTION OF THE DRAWINGS

In the following the invention will be described in greater detail with reference to the attached drawings, in which.

DETAILED DESCRIPTION OF THE INVENTION

Figure 1:
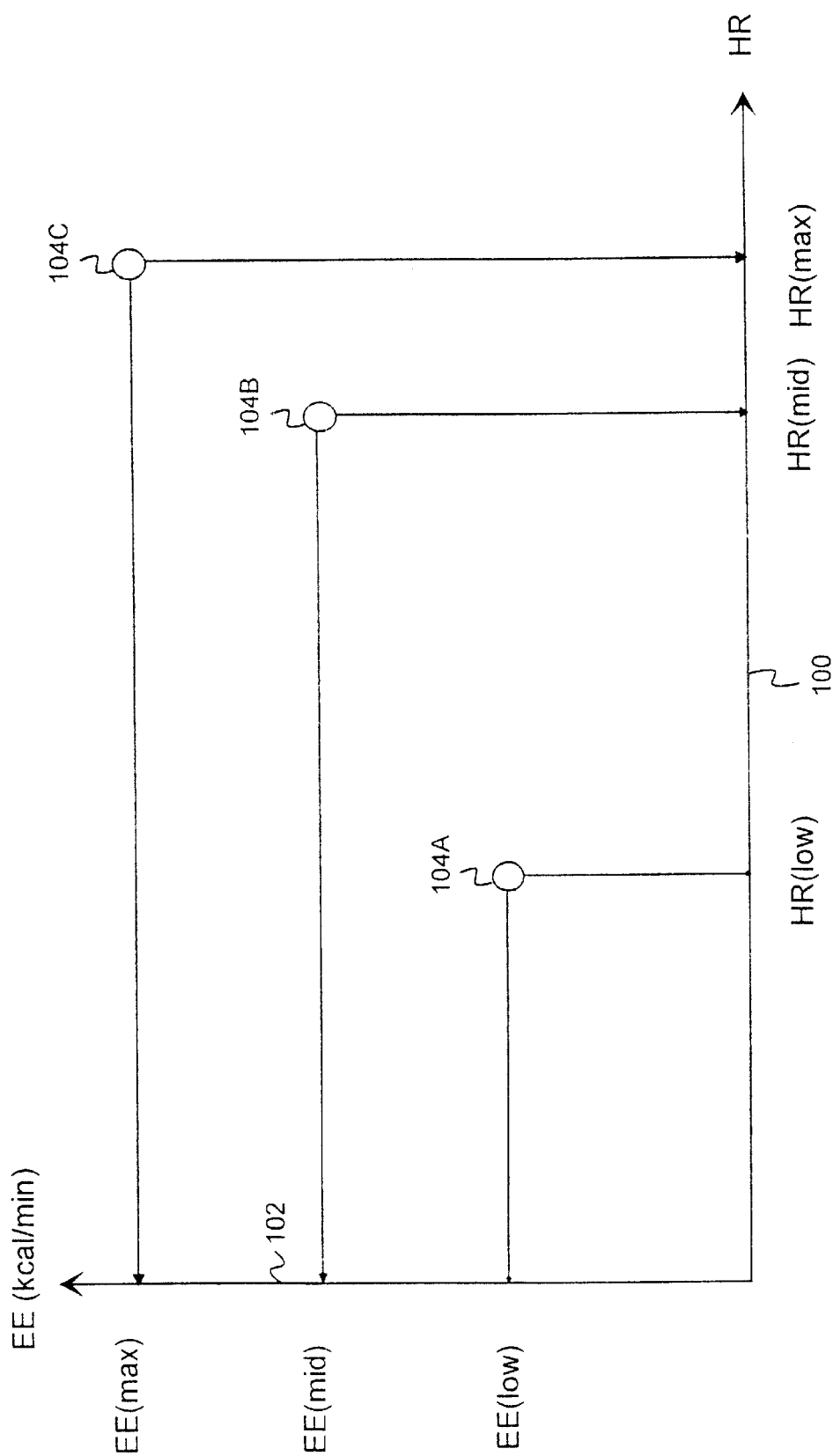
FIG. 1 shows how a model of one embodiment is formed.

In the following the invention will be described by means of preferred embodiments with reference to the attached drawings 1 to 4C. FIG. 1 shows formation of substantial points 104A to 104C that is carried out in a personalizing phase of equipment implementing the method. In FIG. 1, on the horizontal axis 100 appears heart rate HR, as a function of which on the vertical axis 102 appears a person's energy consumption EE. The points 104A to 104C represent the person's physical performance as a function of the heart rate, the physical performance parameter being one or more of the following: oxygen uptake, speed or performance. By means of the physical performance parameter values 104A to 104C, in turn, it is possible to form assessments of energy consumption, whereby the dependence between the heart rate and the energy consumption shown in FIG. 1 is obtained.

In the solution of FIG. 1, a maximum value 104C of a fitness variable, such as oxygen uptake, at the maximum heart rate $HR_{max}$ is formed first, for instance, by calculating with a formula 220–age, whereby the maximum heart rate of a 30-year old will be 190. The maximum value 104C of the oxygen uptake is measured during maximum performance on the basis of the breathing gases. It is also possible to form the maximum value 104C by assessment by means of a neural network model. The assessment can be carried out on the basis of mere physiological parameters of a user or by a reference exercise, in which case optionally one or more exercise stress parameters representing the workload of the reference exercise and/or one or more physiological parameters are entered into the neural network in addition to one or more heart rate parameters. The oxygen uptake is indicated by a quantity ml/kg/min, and the maximal oxygen uptake $VO_{2max}$ may vary within the range of 20 to 80 ml/kg/min depending on the user's fitness and physiological properties, for instance, such that a person can be considered fit if his/her $VO_{2max}$ is about 60 ml/kg/min and unfit if his/her $VO_{2max}$ is about 30 ml/kg/min. $EE_{max}$, in turn, can be formed by utilizing the $VO_{2max}$ value formed in the above-described manner according to the formula (1):

$$EE_{max} = [VO_{2max} * Weight * (1,2 * RER + 3,8)]/1000, \quad (1)$$

where RER indicates the proportion of exhaled carbon dioxide to inhaled oxygen, at the maximum performance the proportion being about 1.1. According to the formula (1), the maximum energy consumption $EE_{max}$ of a person whose weight is 80 kg and $VO_{2max}$ 50 ml/kg/min is 20.7 kcal/min. The calculating formula (1) is given by way of example, and it is obvious that if the performance parameter used is e.g. running, swimming or cycling speed or resistance of a bicycle or exercise bike, the oxygen uptake in the equation of the formula (1) should be replaced by any other performance parameter. It is possible to use a plurality of performance parameters in assessing the energy consumption, for instance, the resistance of exercise bike and the oxygen uptake can be used simultaneously.

The above formula (1) is based on the principles of energetics in human physiology. Carbohydrates, fats and protein mainly constitute the energetics. Their use and proportions depend on the condition of the body, the amount of available nutrients and the intensity of exercise. Carbohydrates from food provide glucose that is stored in muscles as glucogen. In glucolysis the glucogen degrades releasing energy in accordance with the formula (2). The degradation of fats into energy takes place correspondingly in accordance with the formula (3), however, it requires more oxygen than that of carbohydrates. It appears from the formulae (2) and (3) that the assessment of the amount of energy consumed can be made on the basis of the breathing gases $O_2$ and $CO_2$.

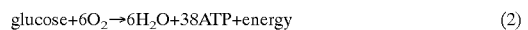
$$glucose + 6O_2 \rightarrow 6H_2O + 38ATP + energy \quad (2)$$
$$fat + 23O_2 \rightarrow 16CO_2 + 16H_2O + 129ATP + energy \quad (3)$$

The point 104A of FIG. 1 is determined next, when the point 104C and the corresponding $EE_{max}$ have been calculated as described above. According to one embodiment of the invention, a lower heart rate $HR_{low}$ is obtained by calculating about 50 to 60% of the $HR_{max}$, i.e. in connection with the present invention the lower heart rate does not refer to the person's resting heart rate but to a rate by which lower energy consumption $EE_{low}$ can be calculated. The $EE_{low}$, in turn, does not refer to the absolute minimum value of energy consumption but to a value, between which value and the maximum value the interdependence of the energy consumption and the heart rate is known. A constant value, such as 100 beats per minute, can also be used as the $HR_{low}$ value for all users. The $HR_{low}$ can also be calculated by the formula $[(HR_{max-HRrest}) * x\%] + HR_{rest}$, where $HR_{rest}$ represents a resting heart rate and x is a predetermined percentage. The $EE_{low}$ corresponding to the $HR_{low}$ is, in turn, obtained by calculating 40% of the $EE_{max}$. The $EE_{low}$ can also be determined by measuring the oxygen consumption corresponding to the $HR_{low}$. The interdependence of the heart rate and the energy consumption is known between the points 104A and 104C determined in this manner, i.e. it is substantially linear.

However, use of a third point, i.e. point 104B corresponding to an intermediate heart rate level $HR_{mid}$, further improves the result of calculation. The $HR_{mid}$ is determined by calculating about 85% of the $HR_{max}$, the point whose counterpart on the y-axis 102 is $EE_{mid}$ which is about 75% of the $EE_{max}$. The point 104B moves horizontally, depending on the person's fitness level, such that an unfit person has this point rather accurately between the points 104A and 104C, whereas the point 104B of a fit person has moved more to the right. When the intermediate heart rate level $HR_{mid}$ is used, the straight line between the points 104A and 104C is piecewise linear such that the space between the points 104A and 104B is substantially linear and the space between the points 104B and 104C is substantially linear. Correct positioning of the point 104B can be taken into account, for instance, such that the person's fitness level is inferred from the $VO_{2max}$ and consequently a higher percentage of the $HR_{max}$ is used for a fit person than an unfit person as the $HR_{mid}$ is calculated. Another alternative way to take the fitness level into account as regards the intermediate point is to keep the $HR_{mid}$ in place and shift the $EE_{mid}$ point upwardly or downwardly depending on the fitness. The $EE_{mid}$ of a fit person is lower than that of an unfit person.

The above-described steps are performed in the personalizing phase of the method, in which one or more calculating parameters are formed, on the basis of which an assessment of energy consumption is formed in the use phase, i.e. during exercise. Energy consumption in the use phase, in which the dependence between the heart rate and the energy consumption is formed by means of three points, is calculated e.g. by means of the following formulae (4) and (5), of which the formula (4) describes energy consumption between the lower heart rate level and the intermediate heart rate level and the formula (5) describes energy consumption between the intermediate heart rate level and the upper heart rate level. For heart rates below the lower heart rate level the formula (4) can be extrapolated when necessary.

$$EE_1 = EE_{low} + \frac{(HR - HR_{low})(EE_{mid} - EE_{low})}{HR_{mid} - HR_{low}} \quad (4)$$

$$EE_2 = EE_{mid} + \frac{(HR - HR_{mid})(EE_{max} - EE_{low})}{HR_{max} - HR_{mid}} \quad (5)$$

In the use phase, the assessment of energy consumption EE is thus formed by means of the heart rate (HR) and other calculating parameters. The reference values of energy consumption $EE_{low}$, $EE_{mid}$ and $EE_{max}$, as well as the other calculating parameters obtained from the heart rate, are formed in the personalizing phase.

In the following, the method of the invention will be described by means of an embodiment with reference to FIGS. 2A and 2B, of which FIG. 2A describes a personalizing phase prior to exercise and FIG. 2B describes a use phase during exercise. The purpose of the personalizing phase is to set the method and the equipment implementing the method such that they give the best possible results for the assessment of the energy consumption in the use phase. The steps 202 to 208 of the personalizing phase are described in connection with FIG. 1. In one preferred embodiment, one measurement, i.e. measurement of the maximum value of a performance parameter, is performed at the user's maximum heart rate level in the personalizing phase. On the basis of the maximum value of the performance parameter and the maximum heart rate are obtained the maximum energy consumption, the lower heart rate and the corresponding lower energy consumption, and optionally-one or more intermediate heart rate levels and the corresponding intermediate energy consumption.

Figure 2:
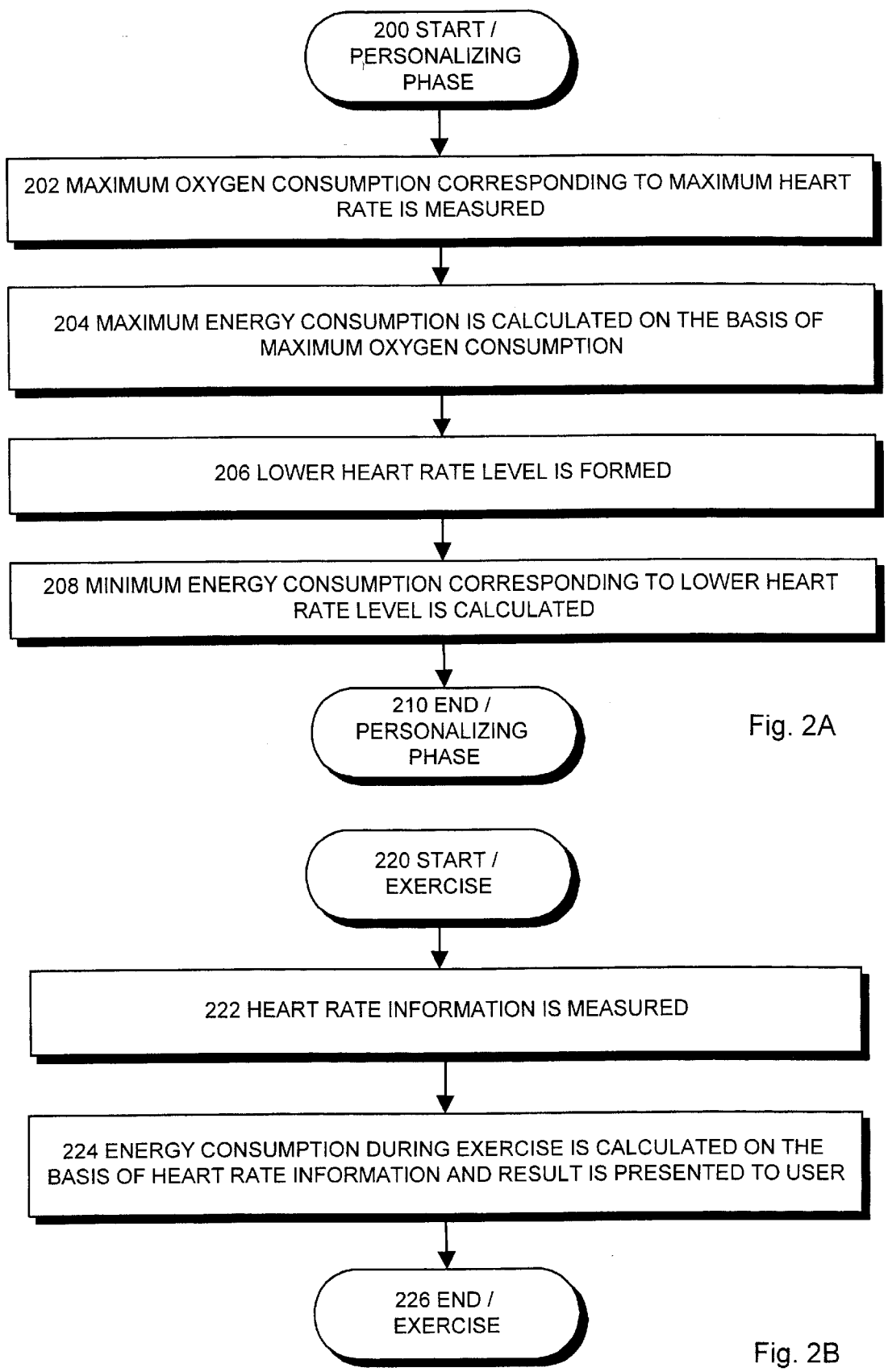
FIG. 2A is a flow chart of one embodiment of the method of the invention.
FIG. 2B is a flow chart of one embodiment of the method of the invention.

FIG. 2B describes the use phase of the method and the equipment implementing the method, such as the heart rate monitor. The use phase is an exercise, an athletic performance, an athletic competition or the like where the heart rate level rises higher than the resting level. The heart rate zone, within which the interdependence of the heart rate and the energy consumption formed in the personalizing phase is known, is typically the heart rate zone exceeding the heart rate level of about 80 beats per minute up to the maximum heart rate. Heart rate information during exercise, such as heart rate frequency, and possibly other parameters calculable from the heart rate, such as the standard deviation of the heart rate and the change rate of the heart rate are measured at the method step 222. At method step 224, an energy consumption value is obtained by calculation, for instance, by the formula (4), which value is presented to the user, exercise instructor, trainer or the like. The energy consumption information to be presented comprises, for instance, cumulative amount of energy consumed from the beginning of exercise or a momentary energy consumption intensity in a time unit, for instance, per minute. Herein, presentation refers to immediate presentation on the display of a heart rate monitor, for instance. Presentation can also be implemented such that the energy consumption information is stored in the memory of the heart rate monitor and transferred to an external computer, where it is downloaded after the exercise, for instance. In one embodiment, the presentation is implemented such that only the heart rate information is stored in the memory during exercise and the energy consumption information is afterwards processed from the heart rate information with an external computer on the basis of the information formed in the personalizing phase.

Figure 3:
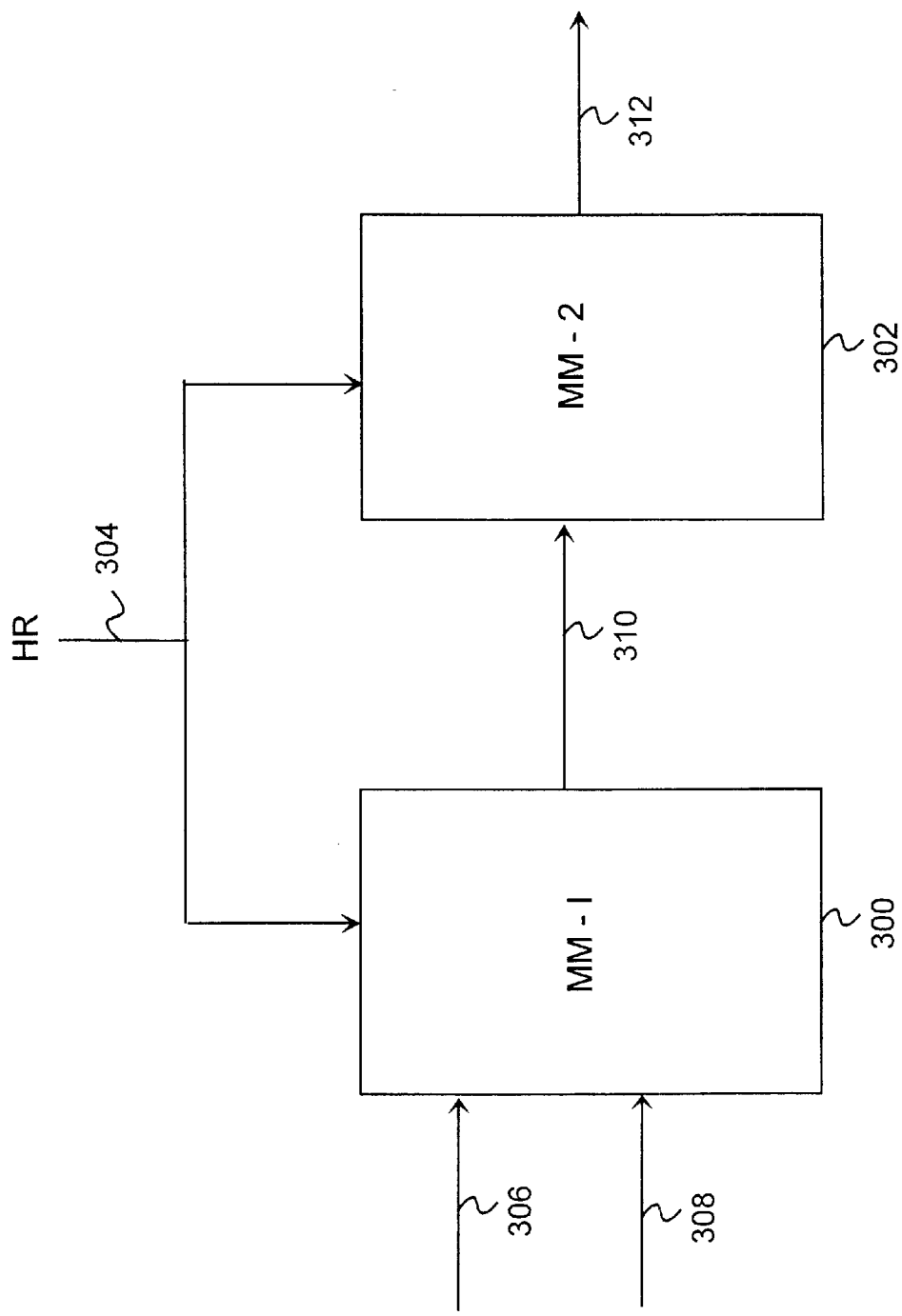
FIG. 3 is a block diagram of a model structure of one embodiment of the invention.

Calculating formulae according to one embodiment of the invention are illustrated next with reference to FIG. 3. MM-I 300 represents the calculating formula to be used in the personalizing phase for forming a performance parameter value. One embodiment of the MM-I is a mathematical model, such as a neural network. One or more heart rate parameters 304 obtained from the heart rate information are preferably entered into the model as input parameters. In addition, one or more physiological parameters and one or more exercise stress parameters are entered into the model 300 as input parameters. The model 300 provides one or more performance parameters 310 as output parameters. MM-2 302, one embodiment of which is presented in the formulae (4) and (5), represents the model to be employed in the use phase during exercise. Heart rate information 304 and one or more performance parameters 310 formed in the personalizing phase are applied to the calculating formula 302 as input parameters. The formula outputs energy consumption information 312 which represents cumulative and/or momentary energy consumption.

Figure 4A:
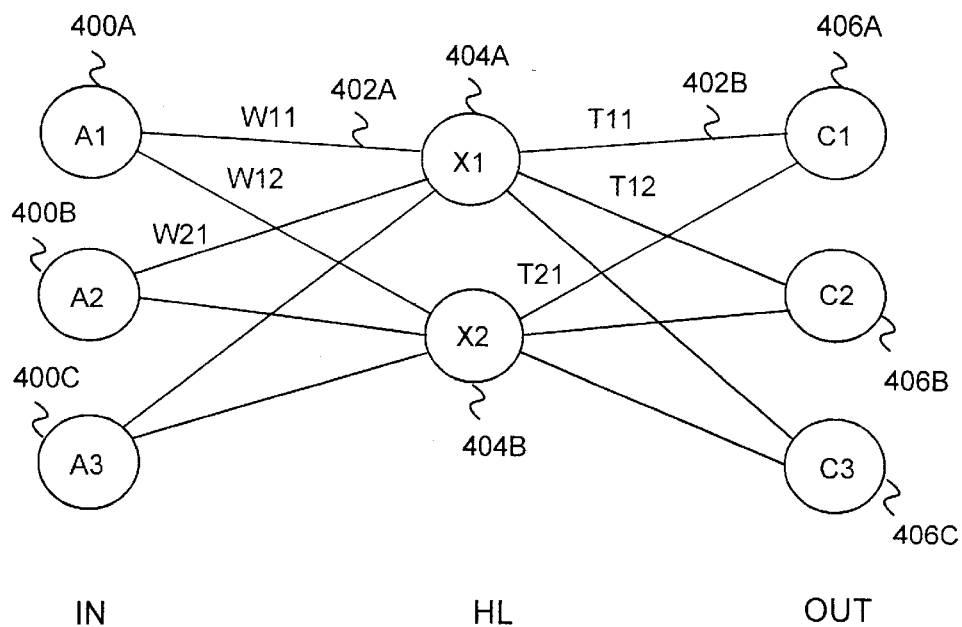
FIG. 4 shows one embodiment of the implementation of a neural network model.
Figure 4B:
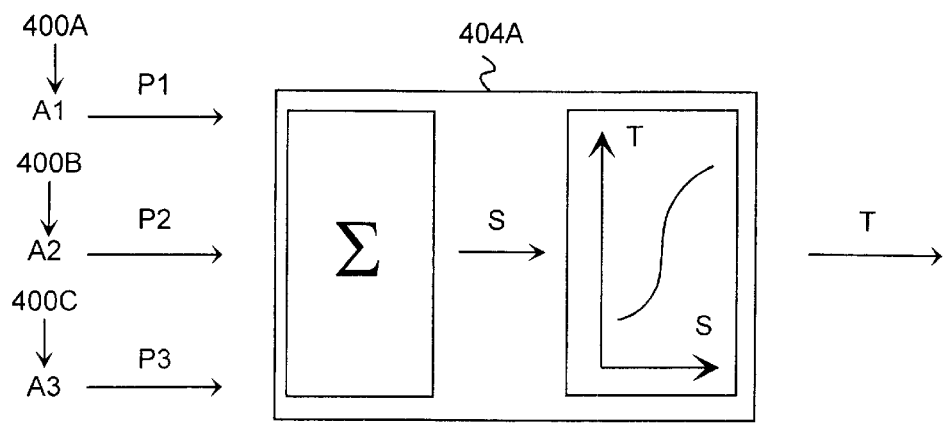

In one embodiment of the invention, the mathematical model implementing the method of the invention is implemented as a neural network whose operational principle is described by means of FIGS. 4A and 4B. The neural network is a way to model complex applications, such as image and speech identification, applications in robotics and applications in physiological analysis, the presentation of which is very difficult as a mathematical model. With reference to FIG. 4A, a neural network comprises neurons, for instance 400A to 400C, 404A to 404B, having a large number of interdependencies, for instance 402A to 402B. The interdependencies 402A to 402B of neurons are referred to as synapses, and a weighting coefficient, for instance W11, W12, is determined for each synapse. The neurons, i.e. nodes, can perform simple calculations, such as the neuron 404A calculating the sum, weighted by weighting coefficients, of the synapses of a previous layer. The neural network comprises at least an input layer, which includes the neurons 400A to 400C, and an output layer, which includes the neurons 406A to 406C. As the performance of the two-layer neural network is rather limited, the neural network advantageously comprises at least one hidden layer HL, which includes the neurons 404A to 404B. There is no synapse between the neurons of the same layer, but the node has a synapse with all the neurons of the adjacent layers. FIG. 4B shows the structure of one neuron 404A in greater detail. The neuron 404A is inputted with respective input parameters 400A to 400C, weighted by weighting coefficients P1 to P3, for which input parameters the neuron forms a weighted sum S. The neuron applies the sum S to an activation function, which is typically a non-linear function of sigmoidal type. The neuron 404A outputs the final value T, and if said final value is delivered to the synapse 402B of FIG. 4A, it is multiplied by the weighting coefficient T11, whereas, if said final value is delivered to the node 406B, it is multiplied by the weighting coefficient T12.

Training is an essential feature of the neural network. In a particular training phase, actual input and output values are presented to the model, and the model compares them with the calculated output values. A difference between the actual and calculated values, i.e. error, is processed in the model, which processing results in tuning the coefficients of the synapses so as to minimize the error. As a consequence of the training phase, the weight of significant synapses increases and the weight of less significant synapses becomes low.

In the following, the equipment implementing the method steps of the invention is described by means of an exemplary embodiment with reference to FIG. 5. The heart rate of a person performing an exercise is measured by means of a transmitter electrode belt fitted around the chest, a whole consisting of device parts 500 A to 508 representing said transmitter electrode belt. Advantageously the measured heart rate is transmitted inductively to a wrist-worn receiver represented by a whole consisting of device parts 520 to 532. The whole formed by the transmitter electrode belt and the receiver is called a heart rate monitor. The operations belonging both to the personalizing phase and the use phase of the method of the invention are also performed by the heart rate monitor.

The transmitter electrode belt measures heart rate information by means for measuring heart rate information 500A to 500B. The measuring means are, for instance, electrodes which the heart rate monitor comprises at least two but they may be more. From the electrodes 500A to 500B the heart rate signal is applied to an ECG preamplifier 502, wherefrom the signal is transferred via an AGC amplifier 504 and a power amplifier 506 to a transmitter 508. The transmitter 508 is advantageously implemented as a coil which sends the heart rate information 510 inductively to a receiver, such as a wrist-worn receiver unit or an external computer, for instance. One 5 kHz burst 510A corresponds to one heart beat, for instance, or a cluster of a plurality of bursts 510A to 510C may correspond to one beat. The intervals 512A to 512B of bursts 510A to 510C can be equal in length or mutually different in length. Information between the electrode belt and the receiver unit can be transmitted inductively, or alternatively, optically or via a conductor, for instance. The receiver unit 520 to 532, such as the wrist-worn receiver, comprises in one embodiment a receiver coil 520, from which the received signal is applied through a signal receiver 522 to a central processor 524, which coordinates the operation of the different parts of the receiver unit. Advantageously, the receiver unit also comprises a memory 528 for storing the heart rate information and/or energy consumption information and presenting means 530 for presenting the heart rate or the heart rate variables derived therefrom, such as the standard deviation. By the presenting means 530 it is also possible to display to the user information that is relevant in view of the method of the invention, such as the cumulative energy consumption from the beginning of the exercise and/or momentary energy consumption in a time unit. The presenting means 530 comprise, for instance, a display, a speech controller or means for transmitting the heart rate and/or feedback information to an external computer or data network for presenting them separately from the heart rate monitor. The transmitting means can be implemented, for instance, by an induction coil, an optical transmitter, or a connector for transmission via a connecting line. A heart rate measuring arrangement is in question if the information measured or generated by the heart rate monitor is transmitted to equipment outside the heart rate monitor, such as a computer.

According to a preferred embodiment, the presenting means are then located in the computer, by which the information measured in real-time or stored in the memory 528 of the heart rate monitor can be displayed.

Figure 5:
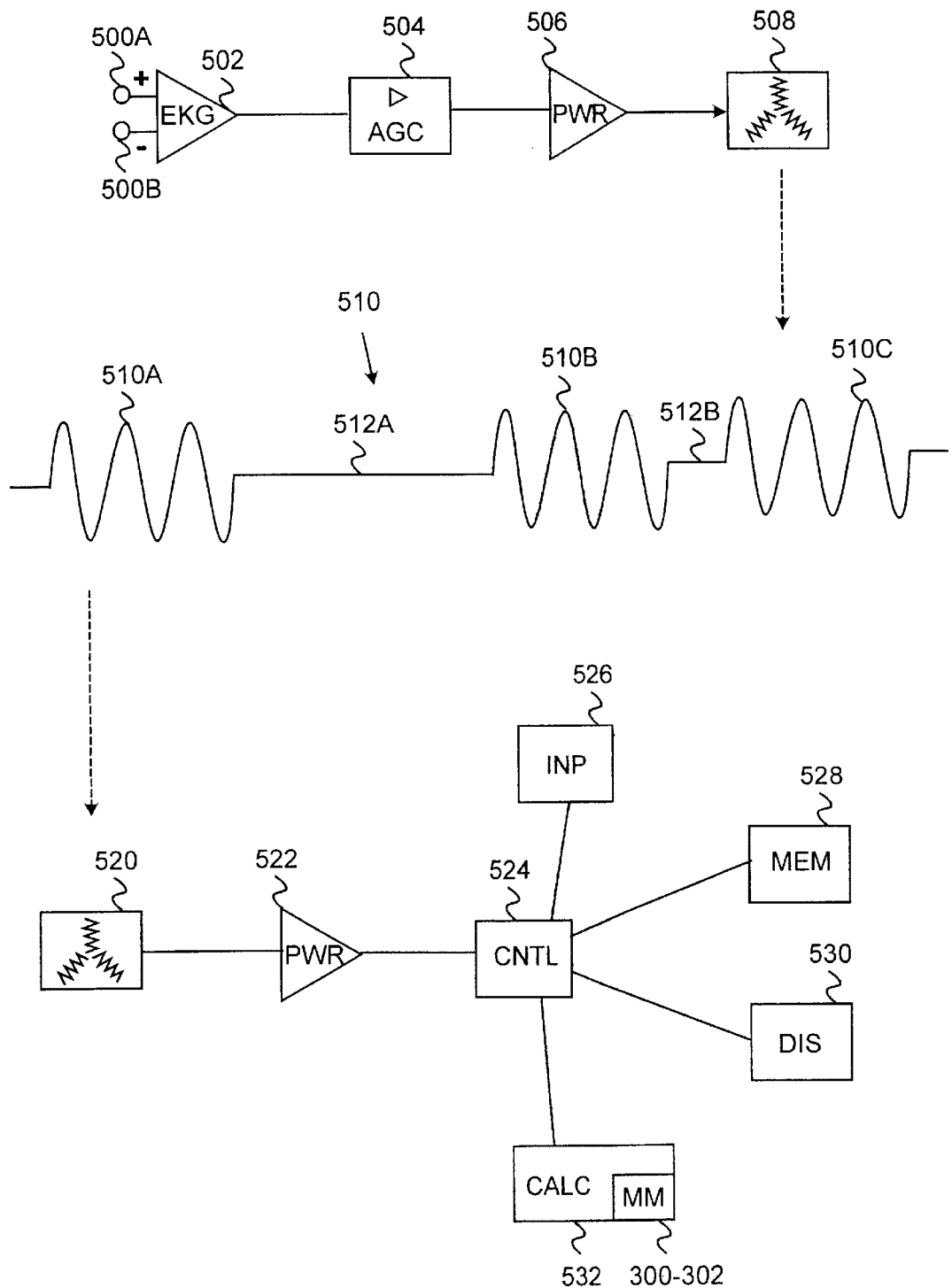
FIG. 5 shows one embodiment of equipment of the invention.

The heart rate monitor and the receiver according to one embodiment thereof, shown in FIG. 5, further comprise a calculating unit 532 for providing an assessment of the energy consumption of the body on the basis of the measured heart rate information. The calculating unit 532 advantageously implements the method steps of the method according to the invention both in the personalizing phase and in the use phase during exercise. The calculating unit 532 thus comprises one or more mathematical models 300 to 302 necessary for the implementation of the method according to the invention. The calculating unit 532 communicates with the central unit 524, through which the calculating unit receives the input parameter values necessary for the calculating operations. The input parameters are entered with entering means 526 of the heart rate monitor, which are e.g. a keypad, a speech controller or a telecommunication port for entering data from external equipment. It is clear that the calculating unit 532 need not be implemented as a separate device part but the functions included therein can be implemented in the central processor 524, for instance.

The functions, means and models implementing the method steps of the invention are implemented, for instance, by means of software for a general-purpose processor, as ASIC, by separate logic components or any corresponding, known manner. It is obvious to a person skilled in the art that the heart rate monitor may also comprise other parts than those in FIG. 5, but it is not relevant to describe them herein.

Even though the invention is described above with reference to the examples of the attached drawings, it is obvious that the invention is not restricted thereto but it can be modified in a variety of ways within the scope of the inventive idea of the attached claims.

What is claimed is:

1. A method for assessing a person's energy consumption during exercise, the method comprising the steps of:
   measuring the person's heart rate information during exercise, the heart rate information including a heart rate parameter;
   obtaining an energy consumption reference value from one or more performance parameters that describe the person's physical performance with at least one of the performance parameters being oxygen uptake;
   assessing the person's energy consumption by means of a plurality of calculating parameters including at least the heart rate parameter and the energy consumption reference value.

2. A method as claimed in claim 1, wherein a maximum value of the oxygen uptake is obtained by measuring the oxygen uptake in an exercise corresponding to a maximum value of the heart rate parameter by means of a neural network.

3. A method as claims in claim 1, wherein the energy consumption reference value is obtained from at least one or more physiological parameters which describe the person's physiology.

4. A method as claimed in claim 1, the performance parameters include at least one of speed and capacity.

5. A method as claimed in claim 1, wherein the plurality of calculating parameters include at least a maximum value of energy consumption and a lower value of energy consumption, wherein the person's energy consumption on the heart rate parameter is substantially linear dependent between the maximum value of energy consumption and the lower value of energy consumption.

6. A method as claimed in claim 1, wherein the plurality of calculating parameters include at least a maximum value of energy consumption, an intermediate value of energy consumption, and a lower value of energy consumption, wherein the person's energy consumption on the heart rate parameter is substantially linear dependent between the intermediate value of energy consumption and one of: the maximum value of energy consumption; and the lower value of energy consumption.

7. A method as claimed in claim 5, wherein the lower value of energy consumption is obtained by calculating about 40% of the maximum value of energy consumption.

8. A method as claimed in claim 6, wherein the lower value of energy consumption is obtained by calculating about 40% of the maximum value of energy consumption.

9. A method as claimed in claim 6, wherein the intermediate value of energy consumption is obtained by calculating about 75% of the maximum value of energy consumption.

10. A method as claimed in claim 8, wherein the intermediate value of energy consumption is obtained by calculating about 75% of the maximum value of energy consumption.

11. A method as claimed in claim 1, wherein the plurality of calculating parameters include at least one of: a maximum heart rate corresponding to the person's maximum performance, a lower heart rate lower than the maximum heart rate, and an intermediate heart rate which is between the maximum heart rate and the lower heart rate.

12. A method as claimed in claim 11, wherein the maximum heart rate is obtained by at least one of:
  assessing;
  measuring the heart rate under the maximum exercise stress;
  assessing on the basis of the person's age; and
  forming an assessment by means of a neural network model into which at least one physiological parameter representing the person's physiology is entered as an input parameter.

13. A method as claimed in claim 11, wherein the lower heart rate is obtained by at least one of:
  assessing;
  calculating about 50 to 60% of the maximum heart rate; and
  making an assessment on the basis of the person's resting heart rate.

14. A method as claimed in claim 11, wherein the intermediate heart rate is obtained by at least one of:
  assessing;
  calculating about 85% of the maximum heart rate; and
  calculating about 85% of the upper heart rate and précising the assessment on the basis of the person's physical condition.

15. A method as claimed in claim 1, wherein the measuring of the heart rate information is measured with a heart rate monitor having a display, the heart rate monitor forming an assessment of the person's energy consumption based on the heart rate information; and the method further comprising the step of:
  displaying the assessment on the display of the heart rate monitor.

16. A heart rate measuring arrangement comprising:
  a measuring means for measuring a person's heart rate;
  a calculating unit for calculating an assessment of the person's energy consumption during exercise from a plurality of calculating parameters, the plurality of calculating parameters including the heart rate and an energy consumption reference value, the energy consumption reference value being obtained from one or more performance parameters that describe the person's physical performance with at least one of the performance parameters being oxygen uptake; and
  a presenting means for presenting the formed assessment of the person's energy consumption.

17. A heart rate measuring arrangement as claimed in claims 16, wherein the calculating unit is arranged to use as a maximum value of the oxygen uptake that is measured in an exercise corresponding to the maximum heart rate.

18. A heart rate measuring arrangement as claimed in claim 16, wherein the calculating unit is arranged to use as a maximum value of the oxygen uptake obtained by means of a neural network.

19. A heart rate measuring arrangement as claimed in claim 16, wherein the energy consumption reference value is formed by the calculating unit using one or more physiological parameters that represent the person's physiology.

20. A heart rate measuring arrangement as claimed in claim 16, wherein the performance parameters include at least one of speed and capacity.

21. A heart rate measuring arrangement as claimed in claim 16, wherein the plurality of calculating parameters include at least a maximum value of energy consumption and a lower value of energy consumption, wherein the person's energy consumption on the heart rate parameter is substantially linear dependent between the maximum value of energy consumption and the lower value of energy consumption.

22. A heart rate measuring arrangement as claimed in claim 16, wherein the plurality of calculating parameters include at least a maximum value of energy consumption, an intermediate value of energy consumption, and a lower value of energy consumption, wherein the person's energy consumption on the heart rate parameter is substantially linear dependent between the intermediate value of energy consumption and one of: the maximum value of energy consumption; and the lower value of energy consumption.

23. A heart rate measuring arrangement as claimed in claim 21, wherein the calculating unit is arranged to generate the lower value of energy consumption by calculating about 40% of the maximum value of energy consumption.

24. A heart rate measuring arrangement as claimed in claim 22, wherein the calculating unit is arranged to generate the lower value of energy consumption by calculating about 40% of the maximum value of energy consumption.

25. A heart rate measuring arrangement as claimed in claim 22, wherein the calculating unit is arranged to generate the intermediate value of energy consumption by calculating about 75% of the maximum value of energy consumption.

26. A heart rate measuring arrangement as claimed in claim 25, wherein the calculating unit is arranged to generate the intermediate value of energy consumption by calculating about 75% of the maximum value of energy consumption.

27. A heart rate measuring arrangement as claimed in claim 16, wherein the plurality of calculating parameters include at least one of: a maximum heart rate corresponding to the person's maximum performance, a lower heart rate lower than the maximum heart rate, and an intermediate heart rate which is between the maximum heart rate and the lower heart rate.

28. A heart rate measuring arrangement as claimed in claim 27, wherein the calculating unit is arranged to use the maximum heart rate formed by at least one of:
  an assessed heart rate;

the heart rate measured during exercise corresponding to a maximum exercise stress;

assessment based on the person's age; and made by means of a neural network model into which at least one physiological parameter representing the person's physiology is entered as an input parameter.

29. A heart rate measuring arrangement as claimed in claim 27, wherein the calculating unit is arranged to use the lower heart rate formed by at least one of:

an assessed heart rate;

a heart rate calculated about 50 to 60% of the maximum heart rate; and an assessment made on the basis of the person's resting heart rate.

30. A hear rate measuring arrangement as claimed in claim 27 wherein the calculating unit is arranged to use the intermediate heart rate formed by at least one of:

an assessed heart rate;

an intermediate heart rate calculated about 85% of the maximum heart rate; and an assessment calculated about 85% of the upper heart rate level and précised on the basis of the person's physical condition.

31. A heart rate measuring arrangement as claimed in claim 16, wherein the presenting means are a display.

* * * * *

UNITED STATES PATENT AND TRADEMARK OFFICE
CERTIFICATE OF CORRECTION

PATENT NO.    : 6,537,227 B1
DATED         : March 25, 2003
INVENTOR(S)   : Kinnunen et al.

It is certified that error appears in the above-identified patent and that said Letters Patent is hereby corrected as shown below:

Column 12,
Line 9, "A heart rate measunng arrangement" should read
-- A heart rate measuring arrangement --

Signed and Sealed this

Twenty-ninth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,537,227 B1
DATED : March 25, 2003
INVENTOR(S) : Kinnunen et al.

It is certified that error appears in the above-identified patent and that said Letters Patent is hereby corrected as shown below:

<u>Title page,</u>
Item [30], Foreign Application Priority Data, now reads
"March 7, 2000 (FI).....................000522" should read
-- March 7, 2000 (FI).................20000522 --

Signed and Sealed this

Twenty-eighth Day of October, 2003

JAMES E. ROGAN
*Director of the United States Patent and Trademark Office*

US 6,537,227 C1

(12) EX PARTE REEXAMINATION CERTIFICATE (9694th)
United States Patent
Kinnunen et al.

(10) Number: US 6,537,227 C1
(45) Certificate Issued: Jun. 4, 2013

(54) METHOD AND EQUIPMENT FOR HUMAN-RELATED MEASURING

(75) Inventors: Hannu Kinnunen, Oulu (FI); Seppo Nissilä, Oulu (FI)

(73) Assignee: Polar Electro Oy, Kempele (FI)

Reexamination Request:
No. 90/012,514, Sep. 12, 2012

Reexamination Certificate for:
Patent No.: 6,537,227
Issued: Mar. 25, 2003
Appl. No.: 09/798,577
Filed: Mar. 2, 2001

Certificate of Correction issued Jul. 29, 2003
Certificate of Correction issued Oct. 28, 2003

(30) Foreign Application Priority Data

Mar. 7, 2000 (FI) ..................................... 20000522

(51) Int. Cl.
*A61B 5/02* (2006.01)
(52) U.S. Cl.
USPC ............................ 600/500; 600/483; 600/508

(58) Field of Classification Search
None
See application file for complete search history.

(56) References Cited

To view the complete listing of prior art documents cited during the proceeding for Reexamination Control Number 90/012,514, please refer to the USPTO's public Patent Application Information Retrieval (PAIR) system under the Display References tab.

*Primary Examiner* — Jeffrey R Jastrzab

(57) ABSTRACT

A heart rate measuring arrangement comprising measuring means (500A to 500B) for measuring a person's heart rate during exercise and a calculating unit (532) for calculating an assessment of the person's energy consumption during exercise using at least two calculating parameters, one of which is a heart rate parameter included in the person's measured heart rate information, the heart rate measuring arrangement further comprising presenting means (530) for presenting the formed assessment of the person's energy consumption. The calculating unit is arranged to use an energy consumption reference value as a calculating parameter, which reference value is obtained by using one or more performance parameters representing the person's physical performance.

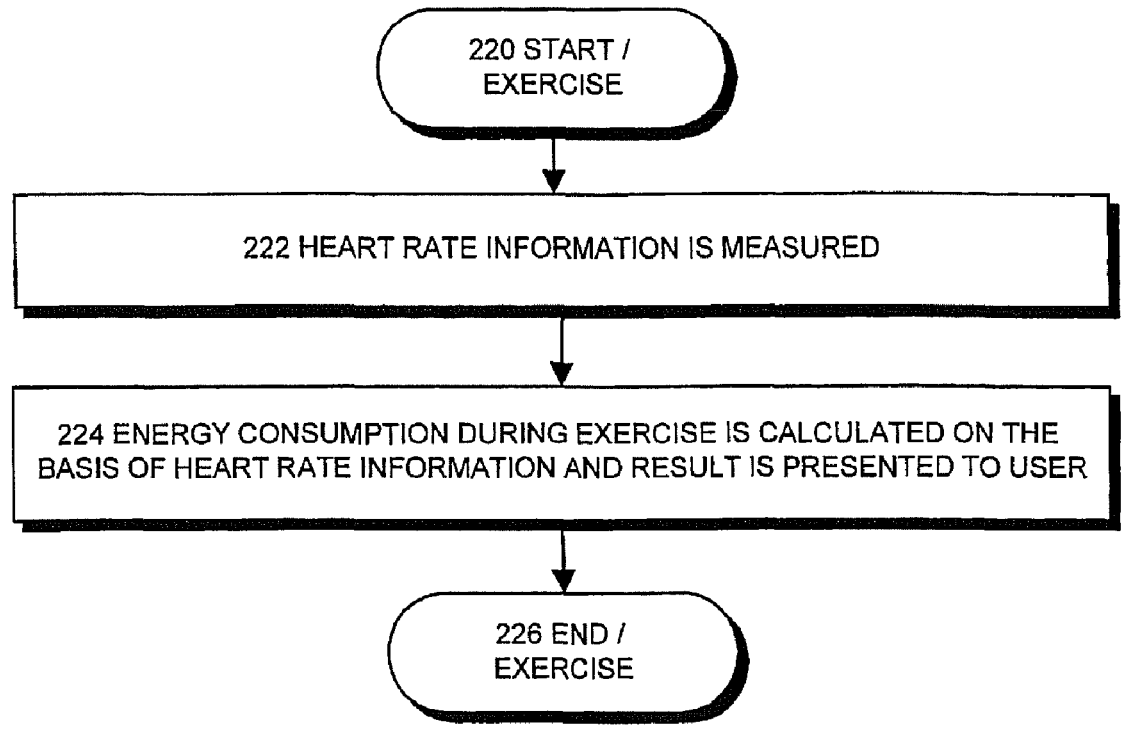

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 16 are cancelled.

Claims 2-6, 11, 15, 17-22, 27 and 31 are determined to be patentable as amended.

Claims 7-10, 12-14, 23-26 and 28-30, dependent on an amended claim, are determined to be patentable.

New claims 32-42 are added and determined to be patentable.

2. A method as claimed in claim [1] *5*, wherein a maximum value of the oxygen uptake is obtained by measuring the oxygen uptake in an exercise corresponding to a maximum value of the heart rate parameter by means of a neural network.

3. A method as claims in claim [1] *5*, wherein the energy consumption reference value is obtained from at least one or more physiological parameters which describe the person's physiology.

4. A method as claimed in claim [1] *5*, *wherein* the performance parameters include at least one of speed and capacity.

5. A method [as claimed in claim 1] *for assessing a person's energy consumption during exercise, the method comprising the steps of:*

*measuring the person's heart rate information during exercise, the heart rate information including a heart rate parameter;*

*obtaining an energy consumption reference value from one or more performance parameters that describe the person's physical performance with at least one of the performance parameters being oxygen uptake;*

*assessing the person's energy consumption by means of a plurality of calculating parameters including at least the heart rate parameter and the energy consumption reference value, wherein the plurality of calculating parameters include at least a maximum value of energy consumption and a lower value of energy consumption, wherein the person's energy consumption on the heart rate parameter is substantially linear dependent between the maximum value of energy consumption and the lower value of energy consumption.*

6. A method [as claimed in claim 1] *for assessing a person's energy consumption during exercise, the method comprising the steps of:*

*measuring the person's heart rate information during exercise, the heart rate information including a heart rate parameter;*

*obtaining an energy consumption reference value from one or more performance parameters that describe the person's physical performance with at least one of the performance parameters being oxygen uptake;*

*assessing the person's energy consumption by means of a plurality of calculating parameters including at least the heart rate parameter and the energy consumption reference value, wherein the plurality of calculating parameters include at least a maximum value of energy consumption, an intermediate value of energy consumption, and a lower value of energy consumption, wherein the person's energy consumption on the heart rate parameter is substantially linear dependent between the intermediate value of energy consumption and one of: the maximum value of energy consumption; and the lower value of energy consumption.*

11. A method as claimed in claim [1] *5*, wherein the plurality of calculating parameters include at least one of: a maximum heart rate corresponding to the person's maximum performance, a lower heart rate lower than the maximum heart rate, and an intermediate heart rate which is between the maximum heart rate and the lower heart rate.

15. A method as claimed in claim [1] *5*, wherein the measuring of the heart rate information is measured with a heart rate monitor having a display, the heart rate monitor forming an assessment of the person's energy consumption based on the heart rate information[;], and the method further comprising the step of[:] displaying the assessment on the display of the heart rate monitor.

17. A heart rate measuring arrangement as claimed in claims [16] *21*, wherein the calculating unit is arranged to use as a maximum value of the oxygen uptake that is measured in an exercise corresponding to the maximum heart rate.

18. A heart rate measuring arrangement as claimed in claim [16] *21*, wherein the calculating unit is arranged to use as a maximum value of the oxygen uptake obtained by means of a neural network.

19. A heart rate measuring arrangement as claimed in claim [16] *21*, wherein the energy consumption reference value is formed by the calculating unit using one or more physiological parameters that represent the person's physiology.

20. A heart rate measuring arrangement as claimed in claim [16] *21*, wherein the performance parameters include at least one of speed and capacity.

21. A heart rate measuring arrangement [as claimed in claim 16] *comprising:*

*a measuring means for measuring a person's heart rate;*

*a calculating unit for calculating an assessment of the person's energy consumption during exercise from a plurality of calculating parameters, the plurality of calculating parameters including the heart rate and an energy consumption reference value, the energy consumption reference value being obtained from one or more performance parameters that describe the person's physical performance with at least one of the performance parameters being oxygen uptake; and*

*a presenting means for presenting the formed assessment of the person's energy consumption, wherein the plurality of calculating parameters include at least a maximum value of energy consumption and a lower value of energy consumption, wherein the person's energy consumption on the heart rate parameter is substantially linear dependent between the maximum value of energy consumption and the lower value of energy consumption.*

22. A heart rate measuring arrangement [as claimed in claim 16] *comprising:*

*a measuring means for measuring a person's heart rate;*

*a calculating unit for calculating an assessment of the person's energy consumption during exercise from a plurality of calculating parameters, the plurality of calculating parameters including the heart rate and an energy consumption reference value, the energy con-* sumption reference value being obtained from one or more performance parameters that describe the person's physical performance with at least one of the performance parameters being oxygen uptake; and a presenting means for presenting the formed assessment of the person's energy consumption, wherein the plurality of calculating parameters include at least a maximum value of energy consumption, an intermediate value of energy consumption, and a lower value of energy consumption, wherein the person's energy consumption on the heart rate parameter is substantially linear dependent between the intermediate value of energy consumption and one of: the maximum value of energy consumption; and the lower value of energy consumption.

27. A heart rate measuring arrangement as claimed in claim [16] *21*, wherein the plurality of calculating parameters include at least one of: a maximum heart rate corresponding to the person's maximum performance, a lower heart rate lower than the maximum heart rate, and an intermediate heart rate which is between the maximum heart rate and the lower heart rate.

31. A heart rate measuring arrangement as claimed in claim [16] *21*, wherein the presenting means are a display.

*32. A method as claimed in claim 6, wherein a maximum value of the oxygen uptake is obtained by measuring the oxygen uptake in an exercise corresponding to a maximum value of the heart rate parameter by means of a neural network.*

*33. A method as claims in claim 6, wherein the energy consumption reference value is obtained from at least one or more physiological parameters which describe the person's physiology.*

*34. A method as claimed in claim 6, wherein the performance parameters include at least one of speed and capacity.*

*35. A method as claimed in claim 6, wherein the plurality of calculating parameters include at least one of: a maximum heart rate corresponding to the person's maximum performance, a lower heart rate lower than the maximum heart rate, and an intermediate heart rate which is between the maximum heart rate and the lower heart rate.*

*36. A method as claimed in claim 6, wherein the measuring of the heart rate information is measured with a heart rate monitor having a display, the heart rate monitor forming an assessment of the person's energy consumption based on the heart rate information, and the method further comprising the step of displaying the assessment on the display of the heart rate monitor.*

*37. A heart rate measuring arrangement as claimed in claims 22, wherein the calculating unit is arranged to use as a maximum value of the oxygen uptake that is measured in an exercise corresponding to the maximum heart rate.*

*38. A heart rate measuring arrangement as claimed in claim 22, wherein the calculating unit is arranged to use as is a maximum value of the oxygen uptake obtained by means of a neural network.*

*39. A heart rate measuring arrangement as claimed in claim 22, wherein the energy consumption reference value is formed by the calculating unit using one or more physiological parameters that represent the person's physiology.*

*40. A heart rate measuring arrangement as claimed in claim 22, wherein the performance parameters include at least one of speed and capacity.*

*41. A heart rate measuring arrangement as claimed in claim 22, wherein the plurality of calculating parameters include at least one of: a maximum heart rate corresponding to the person's maximum performance, a lower heart rate lower than the maximum heart rate, and an intermediate heart rate which is between the maximum heart rate and the lower heart rate.*

*42. A heart rate measuring arrangement as claimed in claim 22, wherein the presenting means are a display.*

\* \* \* \* \*

(12) EX PARTE REEXAMINATION CERTIFICATE (10307th)
United States Patent
Kinnunen et al.

(10) Number: US 6,537,227 C2
(45) Certificate Issued: Oct. 2, 2014

(54) METHOD AND EQUIPMENT FOR HUMAN-RELATED MEASURING

(75) Inventors: Hannu Kinnunen, Oulu (FI); Seppo Nissilä, Oulu (FI)

(73) Assignee: Polar Electro Oy, Kempele (FI)

Reexamination Request:
No. 90/013,140, Jan. 29, 2014

Reexamination Certificate for:
Patent No.: 6,537,227
Issued: Mar. 25, 2003
Appl. No.: 09/798,577
Filed: Mar. 2, 2001

Reexamination Certificate C1 6,537,227 issued Jun. 4, 2013

Certificate of Correction issued Jul. 29, 2003
Certificate of Correction issued Oct. 28, 2003

(30) Foreign Application Priority Data

May 7, 2000 (FI) ..................................... 20000522

(51) Int. Cl.
*A61B 5/02* (2006.01)
(52) U.S. Cl.
USPC ........................... 600/500; 600/483; 600/508

(58) Field of Classification Search
None
See application file for complete search history.

(56) References Cited

To view the complete listing of prior art documents cited during the proceeding for Reexamination Control Number 90/013,140, please refer to the USPTO's public Patent Application Information Retrieval (PAIR) system under the Display References tab.

*Primary Examiner* — William Doerrler

(57) ABSTRACT

A heart rate measuring arrangement comprising measuring means (500A to 500B) for measuring a person's heart rate during exercise and a calculating unit (532) for calculating an assessment of the person's energy consumption during exercise using at least two calculating parameters, one of which is a heart rate parameter included in the person's measured heart rate information, the heart rate measuring arrangement further comprising presenting means (530) for presenting the formed assessment of the person's energy consumption. The calculating unit is arranged to use an energy consumption reference value as a calculating parameter, which reference value is obtained by using one or more performance parameters representing the person's physical performance.

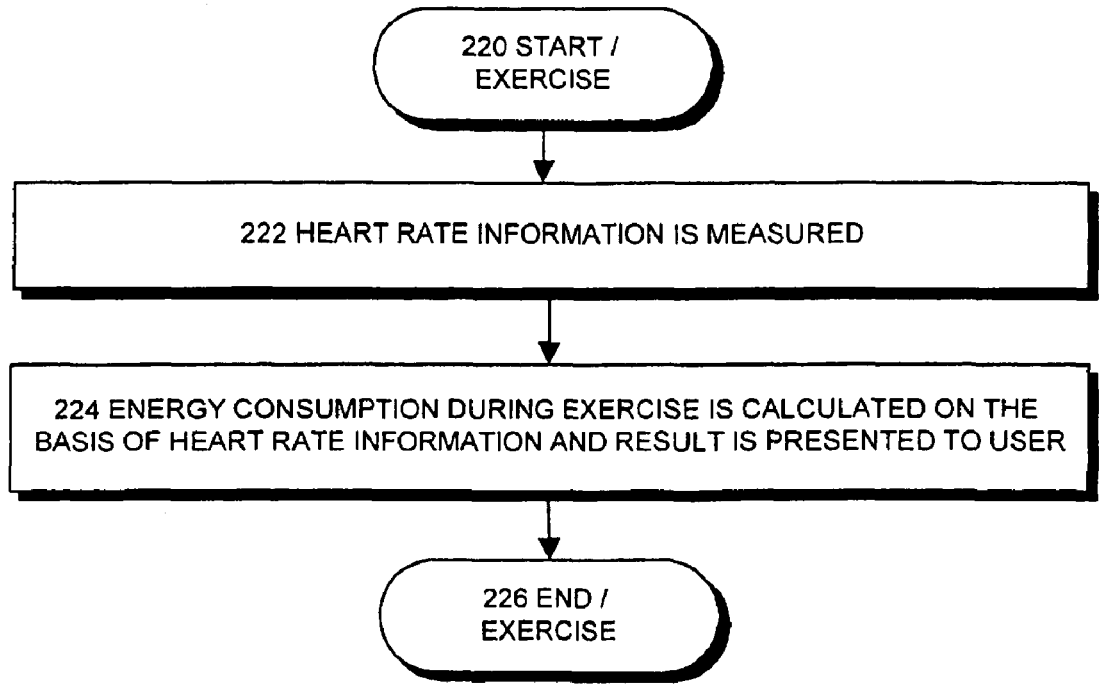

US 6,537,227 C2

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 16 were previously cancelled.

Claims 5, 6, 17, 18, 21, 22, 33, 37 and 38 are determined to be patentable as amended.

Claims 2-4, 7-15, 19, 20, 23-32, 34-36 and 39-42, dependent on an amended claim, are determined to be patentable.

New claims 43-46 are added and determined to be patentable.

5. A method for assessing a person's energy consumption during exercise, the method comprising [the steps of]:
   measuring the person's heart rate information during exercise, the heart rate information including a heart rate parameter;
   obtaining an energy consumption reference value from one or more performance parameters that describe the person's physical performance with at least one of the performance parameters being *a maximal* oxygen uptake, *the energy consumption reference value being a maximum value of energy consumption associated with the person, the maximum value of energy consumption representing a value of energy consumption that is associated with the person and corresponds to a maximum heart rate associated with the person*;
   assessing the person's energy consumption by means of a plurality of calculating parameters including at least the heart rate parameter and the energy consumption reference value, wherein the plurality of calculating parameters include at least [a] *the* maximum value of energy consumption and a lower value of energy consumption, wherein the person's energy consumption *is substantially linear dependent* on the heart rate parameter [is substantially linear dependent] between the maximum value of energy consumption and the lower value of energy consumption.

6. A method for assessing a person's energy consumption during exercise, the method comprising [the steps of]:
   measuring the person's heart rate information during exercise, the heart rate information including a heart rate parameter;
   obtaining an energy consumption reference value from one or more performance parameters that describe the person's physical performance with at least one of the performance parameters being *a maximal* oxygen uptake, *the energy consumption reference value being a maximum value of energy consumption associated with the person, the maximum value of energy consumption representing a value of energy consumption that is associated with the person and corresponds to a maximum heart rate associated with the person*;
   assessing the person's energy consumption by means of a plurality of calculating parameters including at least the heart rate parameter and the energy consumption reference value, wherein the plurality of calculating parameters include at least [a] *the* maximum value of energy consumption, an intermediate value of energy consumption, and a lower value of energy consumption, wherein the person's energy consumption *is substantially linear dependent* on the heart rate parameter [is substantially linear dependent] between the intermediate value of energy consumption and one of[:] the maximum value of energy consumption[;], and the lower value of energy consumption.

17. A heart rate measuring arrangement as claimed in claims 21, wherein the calculating unit is arranged to use [as a maximum value of] the *maximal* oxygen uptake that is measured in an exercise corresponding to the maximum heart rate.

18. A heart rate measuring arrangement as claimed in claim 21, wherein the calculating unit is arranged to use [as a maximum value of] the *maximal* oxygen uptake obtained by means of a neural network.

21. A heart rate measuring arrangement comprising:
   a measuring means for measuring a person's heart rate;
   a calculating unit for calculating an assessment of the person's energy consumption during exercise from a plurality of calculating parameters, the plurality of calculating parameters including the heart rate and an energy consumption reference value, the energy consumption reference value being obtained from one or more performance parameters that describe the person's physical performance with at least one of the performance parameters being *a maximal* oxygen uptake, *the energy consumption reference value being a maximum value of energy consumption associated with the person, the maximum value of energy consumption representing a value of energy consumption that is associated with the person and corresponds to a maximum heart rate associated with the person*; and
   a presenting means for presenting the formed assessment of the person's energy consumption, wherein the plurality of calculating parameters include at least [a] *the* maximum value of energy consumption and a lower value of energy consumption, wherein the person's energy consumption *is substantially linear dependent* on the heart rate parameter [is substantially linear dependent] between the maximum value of energy consumption and the lower value of energy consumption.

22. A heart rate measuring arrangement comprising:
   a measuring means for measuring a person's heart rate;
   a calculating unit for calculating an assessment of the person's energy consumption during exercise from a plurality of calculating parameters, the plurality of calculating parameters including the heart rate and an energy consumption reference value, the energy consumption reference value being obtained from one or more performance parameters that describe the person's physical performance with at least one of the performance parameters being *a maximal* oxygen uptake, *the energy consumption reference value being a maximum value of energy consumption associated with the person, the maximum value of energy consumption representing a value of energy consumption that is associated with the person and corresponds to a maximum heart rate associated with the person*; and
   a presenting means for presenting the formed assessment of the person's energy consumption, wherein the plurality of calculating parameters include at least [a] *the* maximum value of energy consumption, an intermediate value of energy consumption and a lower value of energy consumption, wherein the person's energy consumption *is substantially linear dependent* on the heart rate parameter [is substantially linear dependent] between the intermediate value of energy consumption and one of: the maximum value of energy consumption; and the lower value of energy consumption.

33. A method as [claims] *claimed* in claim 6, wherein the energy consumption reference value is obtained from at least one or more physiological parameters which describe the person's physiology.

37. A heart rate measuring arrangement as claimed in claims 22, wherein the calculating unit is arranged to use [as a maximum value of] the *maximal* oxygen uptake that is measured in an exercise corresponding to the maximum heart rate.

38. A heart rate measuring arrangement as claimed in claim 22, wherein the calculating unit is arranged to use [as is a maximum value of] the *maximal* oxygen uptake obtained by means of a neural network.

*43. A method as claimed in claim 5, wherein the plurality of calculating parameters includes the maximum heart rate associated with the person.*

*44. A method as claimed in claim 6, wherein the plurality of calculating parameters includes the maximum heart rate associated with the person.*

*45. A heart rate measuring arrangement as claimed in claim 21, wherein the plurality of calculating parameters includes the maximum heart rate associated with the person.*

*46. A heart rate measuring arrangement as claimed in claim 22, wherein the plurality of calculating parameters includes the maximum heart rate associated with the person.*

\* \* \* \* \*